United States Patent
Goncalves (10) Patent No.: US 9,144,516 B2
(45) Date of Patent: Sep. 29, 2015

(54) DEVICE FOR INTRAOCULAR ADMINISTRATION OF A SUBSTANCE, FOR EXAMPLE A MEDICATION, INTO A HUMAN OR ANIMAL EYE BY MEANS OF A HYPODERMIC NEEDLE

(75) Inventor: Arnaldo Goncalves, Herten (NL)

(73) Assignee: Sharpsight B.V., Herten (NL)

( * ) Notice: Subject to any disclaimer, the term of this patent is extended or adjusted under 35 U.S.C. 154(b) by 171 days.

(21) Appl. No.: 12/526,399

(22) PCT Filed: Dec. 11, 2007

(86) PCT No.: PCT/NL2007/000312
§ 371 (c)(1),
(2), (4) Date: Aug. 7, 2009

(87) PCT Pub. No.: WO2008/097072
PCT Pub. Date: Aug. 14, 2008

(65) Prior Publication Data
US 2010/0318034 A1    Dec. 16, 2010

(30) Foreign Application Priority Data

Feb. 8, 2007  (NL) .................................. 1033357
Feb. 26, 2007 (NL) .................................. 1033450
Aug. 27, 2007 (NL) .................................. 1034290

(51) Int. Cl.
*A61M 5/00*     (2006.01)
*A61F 9/00*     (2006.01)

(52) U.S. Cl.
CPC ................................ *A61F 9/0017* (2013.01)

(58) Field of Classification Search
CPC ........... A61B 17/0231; A61B 17/3403; A61B 2017/306; A61B 2017/3407; A61F 9/0017
USPC ............ 604/116, 117, 301, 167.04; 606/107, 606/166, 172
See application file for complete search history.

(56) References Cited

U.S. PATENT DOCUMENTS 5,171,254 A * 12/1992 Sher .............................. 606/166
7,470,254 B2 * 12/2008 Basta et al. ............... 604/167.04
(Continued)

FOREIGN PATENT DOCUMENTS

DE         19544119 A1    5/1997
DE      102005002465 A1    7/2006
(Continued)

*Primary Examiner* — Phillip Gray
(74) *Attorney, Agent, or Firm* — Muncy, Geissler, Olds & Lowe, P.C.

(57) ABSTRACT

The invention relates to a device for intraocular administration of a substance, for example a medication, into a human or animal eye by means of a hypodermic needle. Until recently, intravitreal or intraocular injections, by which a substance, and more in particular a medication, is injected into a human or animal eye by means of a hypodermic needle, were only used in exceptional cases. Especially in the treatment of endophthalmitis, an infrequently occurring intraocular inflammation of the eye, antibiotics are often administered intravitreally. The object of the invention is to provide a tool which makes it possible, using one instrument, to keep the eye stationary and at the same time facilitate giving the injection, which will be carried out under identical, reproducible circumstances at all times in that case. According to the invention, the device is characterized in that it comprises a support element to be placed on the eye as well as directing means for orienting the hypodermic needle relative to the eye. Thus it is possible to carry out such eye treatments in an identical, reproducible manner, thereby preventing all kinds of traumas to the eye—resulting from undesirable incorrect insertion of the hypodermic needle—and the associated inconvenience to the patient.

19 Claims, 13 Drawing Sheets

(56) References Cited

U.S. PATENT DOCUMENTS

2001/0008961 A1   7/2001  Hecker et al.
2005/0288697 A1* 12/2005  Tei et al. .................. 606/166
2007/0005016 A1   1/2007  Williams

FOREIGN PATENT DOCUMENTS

| WO | WO-01/49226 A   | 7/2001 |
| WO | WO-03/002010 A1 | 1/2003 |
| WO | WO-2007/052730 A | 5/2007 |

* cited by examiner

DEVICE FOR INTRAOCULAR ADMINISTRATION OF A SUBSTANCE, FOR EXAMPLE A MEDICATION, INTO A HUMAN OR ANIMAL EYE BY MEANS OF A HYPODERMIC NEEDLE

The invention relates to a device for intraocular administration of a substance, for example a medication, into a human or animal eye by means of a hypodermic needle.

Until recently, intravitreal or intraocular injections, by which a substance, and more in particular a medication, is injected into a human or animal eye by means of a hypodermic needle, were only used in exceptional cases. Especially in the treatment of endophtalmitis, an infrequently occurring intraocular inflammation of the eye, antibiotics are often administered intravitreally.

Lately, after the discovery of a new generation of medicines, it has become possible in opthalmology to use intravitreal injections for treating certain eye disorders, which until now could hardly be therapeutically treated, or only to a limited extent. The eye disorders that can thus be treated include: macula degeneration, vena occlusions, diabetes retinopathy, all kinds of macula oedema, neovascular glaucoma, some forms of ischemic eye disorders, etc.

Up to now the medication is injected into the corpus vitreum ("intravitreally"), and the treatment is usually repeated several times. The medication must be administered by an ophthalmologist who has experience giving this kind of injections. Usually, type 25 G-30 G (=Gauge) hypodermic needles are used. The needle is usually inserted into the so-called pars plana at a distance of 3.5 mm from the limbus (the cornea-sclera transition zone).

The eye is held in place by means of tweezers, and the medication is injected into the eye. The position where the hypodermic needle is to be inserted into the eye is usually determined on the basis of the ophthalmologist's visual assessment and experience. An hypodermic needle that is inserted at an incorrect position or at an incorrect angle may cause complications, such as intraocular haemorrhage, or needle damage to the eye lens, which may in turn cause cataracts, retinal detachment and the like.

The object of the invention is to provide a tool which makes it possible, using one instrument, to keep the eye stationary and which at the same time makes it easier to give the injection, which procedure will be carried out under identical, reproducible circumstances at all times in that case.

According to the invention, the device is characterised in that it comprises a support element to be placed on the eye as well as directing means for orienting the hypodermic needle relative to the eye.

Thus it is possible to carry out such eye treatments in an identical, reproducible manner, thereby preventing all kinds of traumas to the eye—resulting from undesirable incorrect insertion of the hypodermic needle—and the associated inconvenience to the patient.

According to a specific embodiment, which makes it possible to place the device on the eye in simple and patient-friendly manner, the support element comprises an annular support surface to be placed on the eye. The annular support surface thus enables a stable placement and orientation of the device on the convex eye surface with a minimal area of contact, so that irritation to the patient's eye is reduced as much as possible.

To achieve a more ergonomic and effective use, the support element comprises a handle. Said handle may be built up of two or more arm handles, which are interconnected with a first end and which are provided at different positions on the support element with their other end.

In order to be able to insert the hypodermic needle into the eye in an identical, reproducible manner when carrying out repeated treatments, the directing means comprise at least one bore formed in the support element, through which the hypodermic needle can be passed. In this way the successive treatments will be carried out under identical circumstances, thus preventing unnecessary trauma to the eye, such as complications resulting from incorrect insertion of the needle, for example intraocular haemorrhage, needle damage to the eye lens, retinal detachment, etc.

More specifically, one embodiment is characterised in that the bore will be spaced 3.5 mm from the cornea-sclera transition zone of the eye at all times when the support element is positioned on the eye. The bore will be oriented perpendicularly to the eye in that case, so as to enable a reproducible placement and insertion of the hypodermic needle. This also prevents unnecessary trauma to the eye or to the patient.

One embodiment furthermore has this functional property that the bore has a diameter corresponding to that of 25 G-30 G hypodermic needles.

According to one embodiment, in order to obtain a reproducible placement of the hypodermic needle relative to the eye, and in particular in order to ensure a constant insertion depth of the needle in the eye, an upright edge functioning as a stop is provided round the bore.

In another specific embodiment of the device according to the invention, the support element comprises an annular support surface to be placed on the eye.

Said support element may be provided with friction-increasing means so as to realise a stable position on the eye. Said friction-increasing means may consist of one or more barbs provided on the support element. This prevents the device from slipping away on the eyeball.

Furthermore, in order to obtain an excellent reproducibility of the successive treatments, the support element is provided with at least one orientation projection to be oriented against the edge of the limbus of the eye.

Another embodiment of the device according to the invention is characterised in that it comprises means arranged for keeping the eye open. Thus, such eye treatments can be carried out in an identical, reproducible manner, in particular using one device, thereby preventing all kinds of traumas to the eye—resulting from the use of two different devices for keeping the eye open and inserting the hypodermic needle—and the associated inconvenience to the patient.

According to a specific embodiment, which makes it possible to keep the eye open in a simple and patient-friendly manner, said means are disposed on either side of the support element. Thus, each eyelid can be kept open in an effective manner, so that the patient's involuntary blinking his or her eyes will not interfere with the insertion of the hypodermic needle. Said means may comprise at least one spreading element to be placed against an eyelid.

To spread the eyelids in a more effective manner, the spreading element extends in the plane of the support element, whilst the spreading element may optionally have a curved shape.

Another embodiment of the device according to the invention is characterised in that the support element is provided with means arranged for moving the conjunctiva that covers the eye relative to the eye temporarily prior to the insertion of the hypodermic needle into the eye.

When the underlying conjunctiva is moved in this manner, there will be no direct open connection between the various eye layers and the outside environment during the treatment. In this way the risk of intraocular inflammation (endophtalmitis) is minimised.

In a specific embodiment, said moving means are provided at the location of the directing means, whilst in another functional embodiment said moving means comprise at least one projection that is directed towards the eye. Said projection projects about 1-2 mm, and it preferably has a bevelled end surface. This prevents undesirable damage to the eye membrane.

The invention will now be explained in more detail with reference to a drawing, in which.

For a better understanding of the invention, corresponding parts shown in the figures will be indicated by the same numerals in the description of the figures below.

Figure 1:
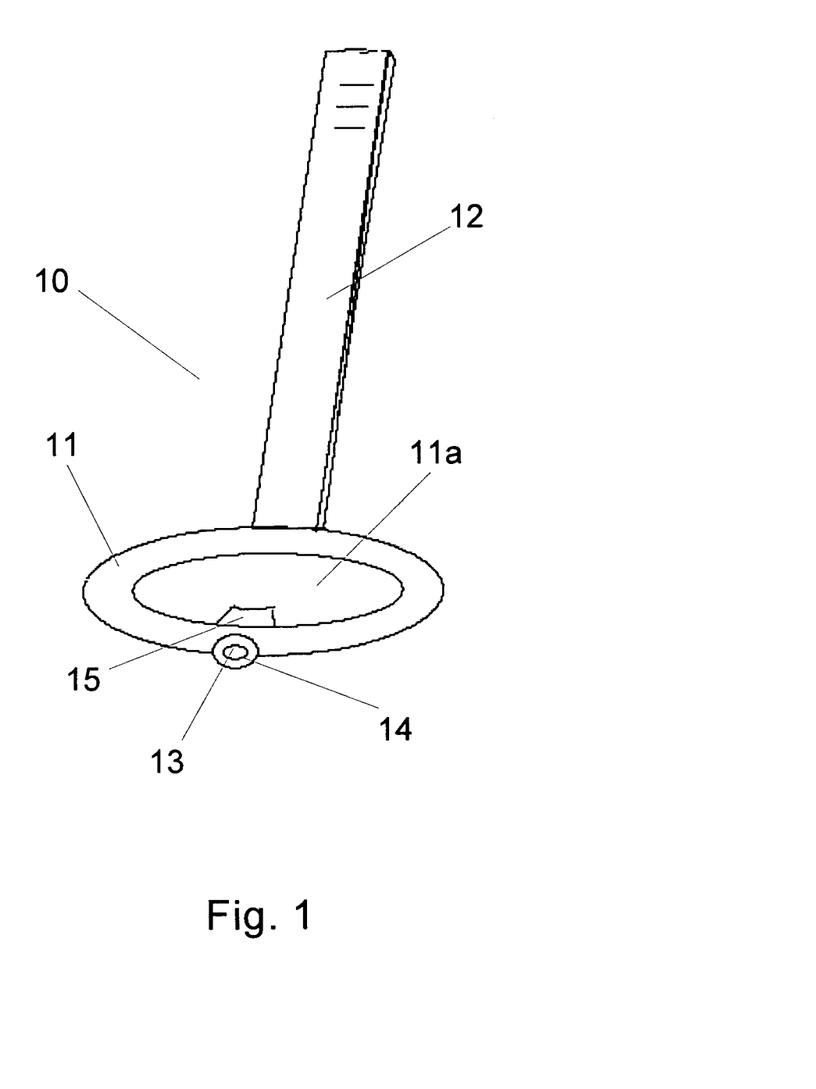
FIG. 1 is a front view of a first embodiment of a device according to the invention.
Figure 2:
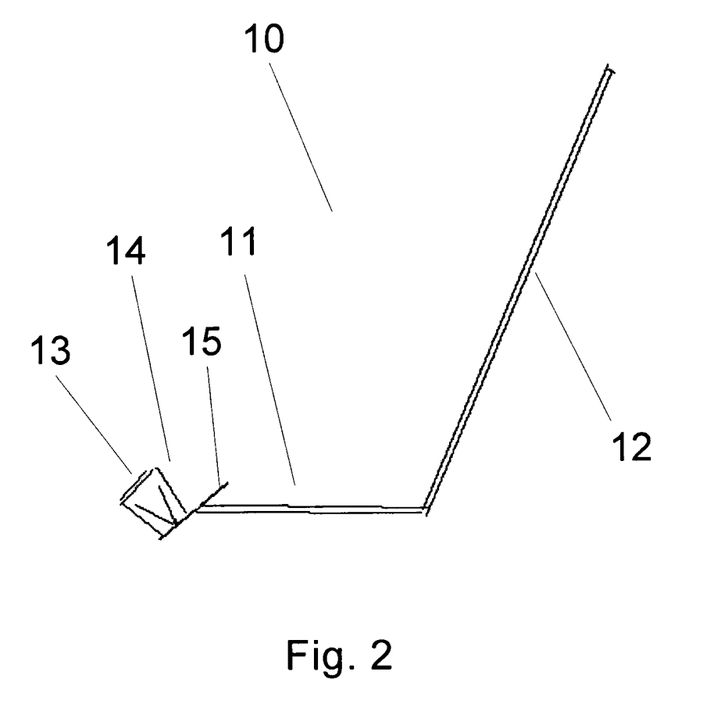
FIG. 2 is a side view of the first embodiment of the device shown in FIG. 1.

FIG. 1 shows a first view of a device according to the invention. The device is made up of a support element 10, which is to be placed on the eye 20 (see FIG. 4a). The support element 10 is provided with directing means 13-14-15 for orienting a hypodermic needle 30-31 (likewise shown in FIG. 4a) relative to the eye 20.

To make it easier for medical staff, for example an ophthalmologist or a surgeon, to manipulate the device, the support element is provided with a handle 12.

To realise an improved orientation, more in particular a reproducible orientation, for inserting the hypodermic needle 31, the support element 11 is configured as an annular support surface to be placed on the eye 20. The annular support surface makes it possible to place the device on the convex eye 20 without irritating the eye 20 unnecessarily. Because of the annular configuration, the contact area with the eye 20 is minimal, so that the patient is protected against trauma and/or irritation.

Figure 4A:
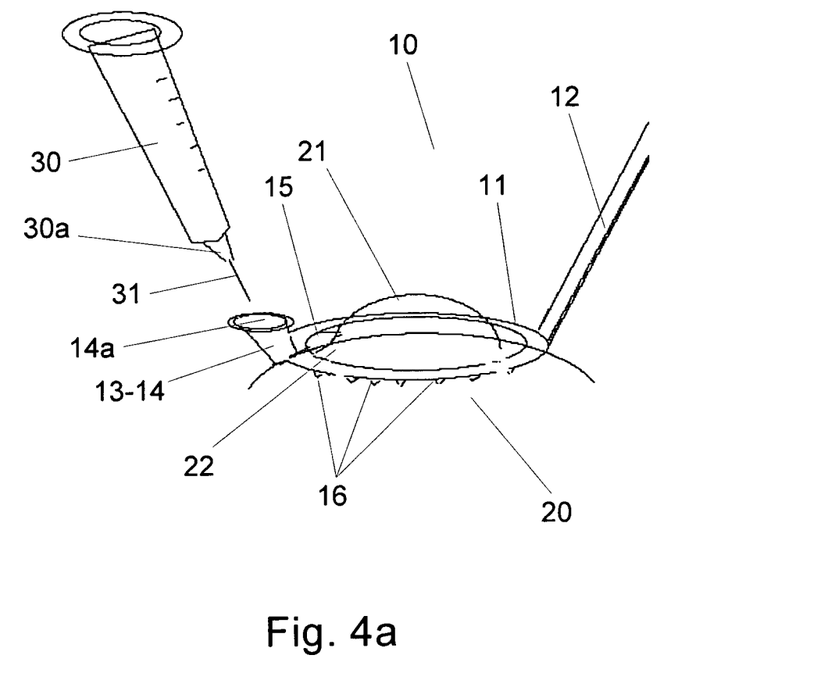
FIGS. 4a and 4b show further detail views of the embodiment of the device shown in FIG. 1.
Figure 4B:
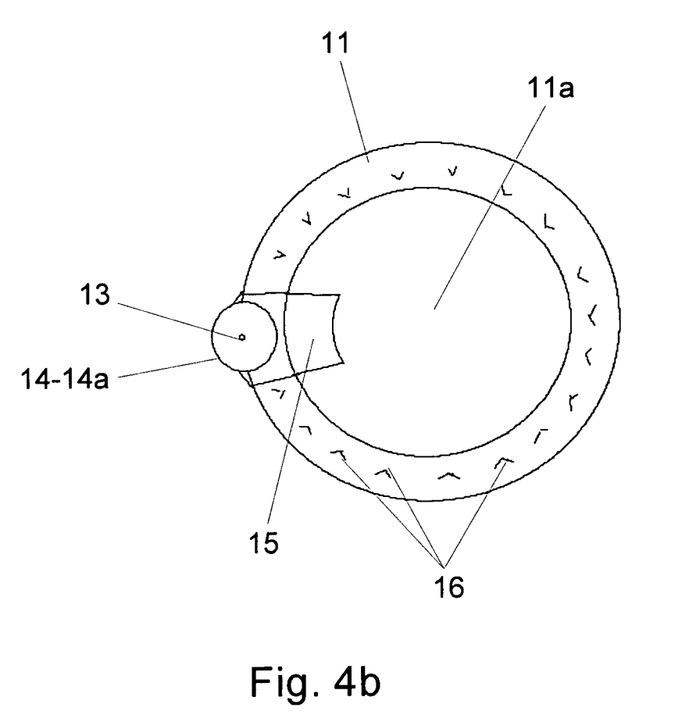

To prevent unnecessary movement of the support element 11 over the eye 20, the annular support element 11 is provided with friction-increasing means, more in particular with barbs 16 as shown in FIGS. 4a and 4b.

To make it possible to carry out repeated medical treatments, viz. inserting a substance, for example a medicine, into the eye 20 by means of the hypodermic needle 31, the directing means 13-14-15 comprise at least one bore 13 formed in the support element, through which the hypodermic needle 31 can be passed. The bore 13 has been formed in the support element 11 in such a manner that the bore, in a first embodiment thereof, takes up a perpendicular orientation relative to the eye surface. In this way a reproducible placement of the device 10 on the eye, and thus an accurate insertion of the hypodermic needle 31 into the eye 20, is ensured at all times. This, too, prevents trauma to the eye or the patient, whilst furthermore preventing the risk of complications resulting from incorrect insertion or insertion at an incorrect angle of the hypodermic needle 31, such as intraocular haemorrhage, needle damage to the eye lens, retinal detachment, etc.

More in particular, the orientation of the bore relative to the eye surface at all times will be identical at all times. The angle between the bore 13 and the eye surface may optionally range between 70° and 95°.

In order to further improve the reproducibility of the medical procedure by means of the instrument 10 according to the invention, the device 10 is so arranged that when the support element 11 is positioned on the eye 20, the bore 13 will be spaced 3.5 mm from the cornea-sclera transition zone of the eye 20 at all times. This positioning is further supported and guaranteed in that the support element 11 is provided with at least one orientation projection 15, which extends on the inner side of the annular support element 11, and whose free end edge is to be placed or oriented against the edge of the limbus of the eye 20 in order to thus position the bore 13 at a distance of 3.5 mm from the cornea-sclera transition zone. The edge of the limbus of the eye 20 is indicated at 22 in FIG. 4a, whilst the eyeball with the lens of the eye 20 is indicated at 21.

The diameter of the bore 13 is selected to accommodate 25 G-30 G hypodermic needles. This makes it possible to use the tool 10 for various hypodermic needles 31 in dependence on the medical treatment to be carried out.

The reproducibility of the medical procedure, but above all the exclusion of unnecessary injury or trauma to the eye 20 can be realised in that an upright edge 14 is provided around the bore 13, which edge functions as a stop for the hypodermic needle 30. This is clearly shown in FIG. 4a, in which the hypodermic needle 31 is inserted into the eye 20 via the space 14a formed by the circular upright edge 14 and the bore 13, whilst the syringe 30 is stopped by the upright edge 14.

Figure 3A:
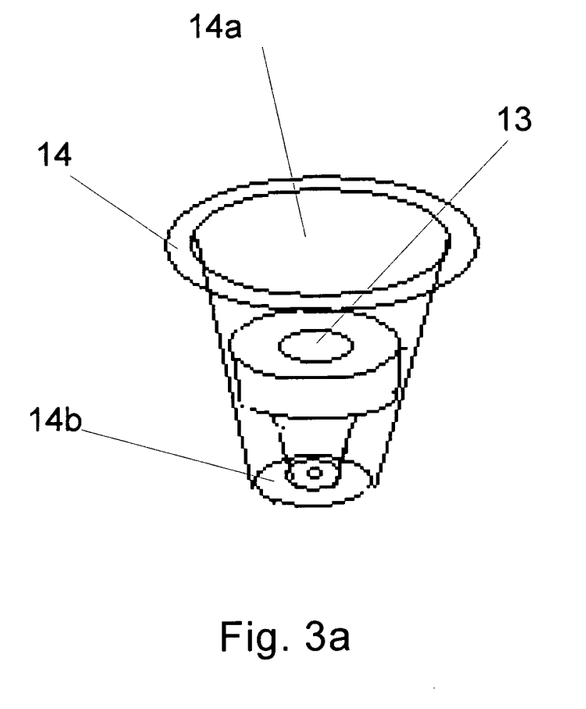
FIGS. 3a and 3b are detail views of the embodiment of the device shown in FIG. 1.
Figure 3B:
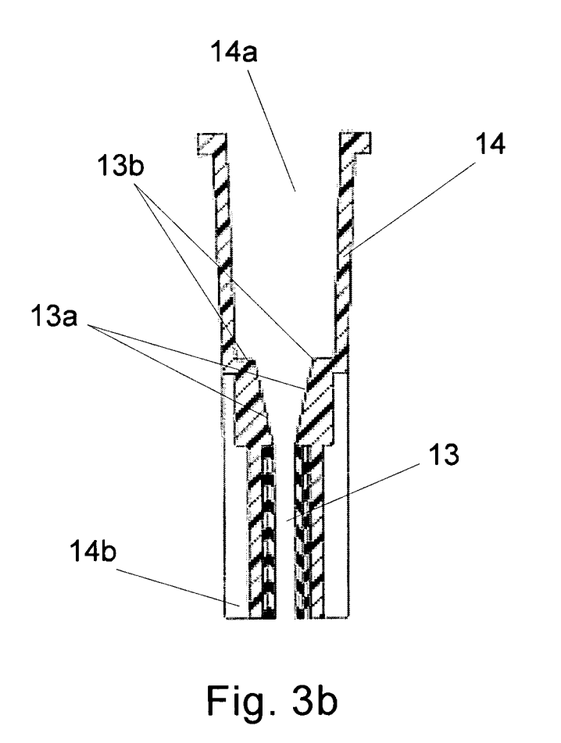

The upright edge 14, which functions as a directing means, is shown in more detail in FIGS. 3a and 3b, in which the upright edge 14 defines a space 14a, whilst numeral 14b indicates an end surface forming part of the support surface of the support element 11, which is supported on the eye 20. The space 14a merges into the bore 13, into which the hypodermic needle 31 can be inserted. The syringe portion 30a of the syringe 30 can be received in the space 14a and will be stopped by the end edge 13b and the bevelled transition edge 13a of the bore 13.

In this way the hypodermic needle 31 can be inserted into the eye 20 to a reproducible, constant depth each time for administering a substance, such as a medication or medicine.

Figure 5:
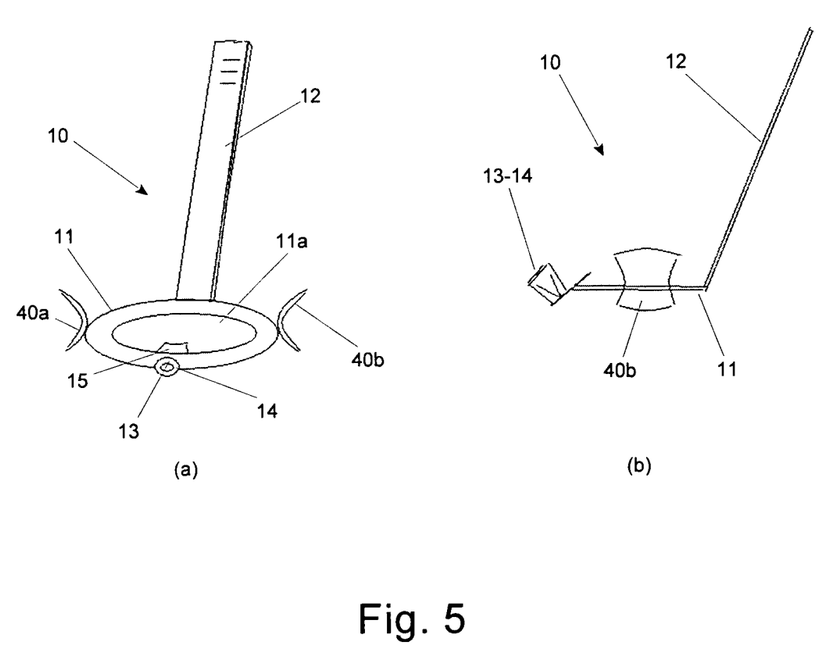
FIGS. 5a and 5b show another aspect of a device according to the invention.

FIGS. 5a and 5b show another embodiment of the device according to the invention. In this embodiment, the device 10 is provided with means 40a-40b arranged for keeping the eye 2 open. More in particular, said means 40a-40b are provided on either side of the support element 11 and comprise a spreading element indicated at 40a-40b, which can be placed into abutment with each eyelid of the eye 20. The spreading element 40a-40b keeps the eye 20, more in particular both eyelids (not shown), of the eye 20 open.

The spreading elements 40a-40b prevent the patient from blinking his or her eye involuntarily and thus disturb the treatment area for the ophthalmologist, resulting in incorrect insertion of the hypodermic needle 30-31 into the eye 20.

More in particular, and as shown in FIG. 5a, each spreading element 40a-40b is configured as a curved element, which on the one hand extends into the plane of the support element 11, but which, in another embodiment thereof, may have an upright shape as shown in FIG. 5a. The eyelids are thus stopped when the eyes are closed involuntarily, so that the treatment area 11a round the support element 11 remains clear for the ophthalmologist.

Figure 6:
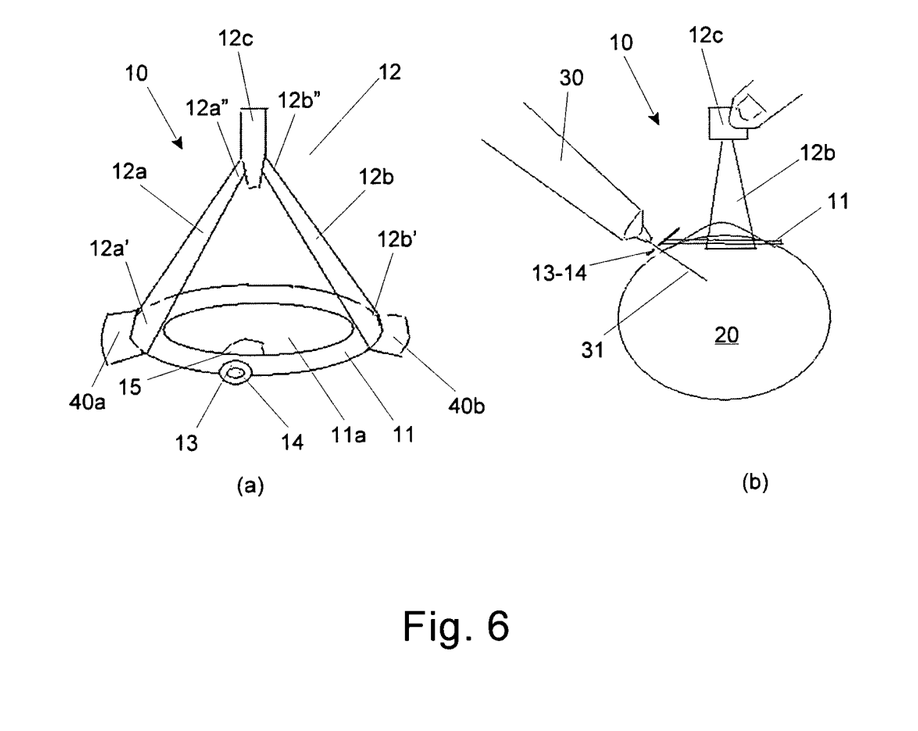
FIGS. 6a and 6b show yet another aspect of a device according to the invention.

FIGS. 6a and 6b show another alternative embodiment of the device 10 according to the invention, in which the handle 12, which is configured as a simple, straight handle in FIGS. 5a-5b, consists of two or more arm handles 12a-12b, which are interconnected with a first end 12a"-12b", forming a gripping element 12c, and which are connected to the support element 11 at different positions with their other end 12a'-12b'.

As is shown in FIGS. 6a-6b, the two arm handles 12a-12b are connected to the support element 11 at the location of each spreading element 40a-40b. Thus, the device 10 as shown in FIG. 6b can be simply held by hand and be manipulated on the eye 20 for inserting a needle 21 by means of the syringe 30 for the purpose of administering a substance or medicine.

Figure 7:
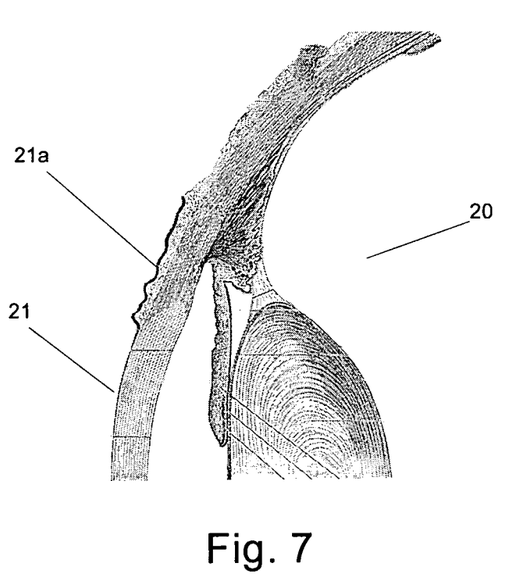
FIG. 7 schematically shows a part of an eye.

FIG. 7 schematically shows a part of the human eye 20 as well as a part of the eyeball 21. Reference numeral 21a indicates the mucous eye membrane, also called the conjunctiva. The conjunctiva covers the eye and functions as a primary protection against dust and other dirt.

With the existing devices, the hypodermic needle pierces the conjunctiva as well as the other eye layers in the eyeball 21 upon insertion thereof. When the hypodermic needle is subsequently withdrawn, a small injection wound remains, which is in direct contact with the outside environment, however. Said injection wound thus involves an increased risk of an intraocular inflammation.

Figure 8:
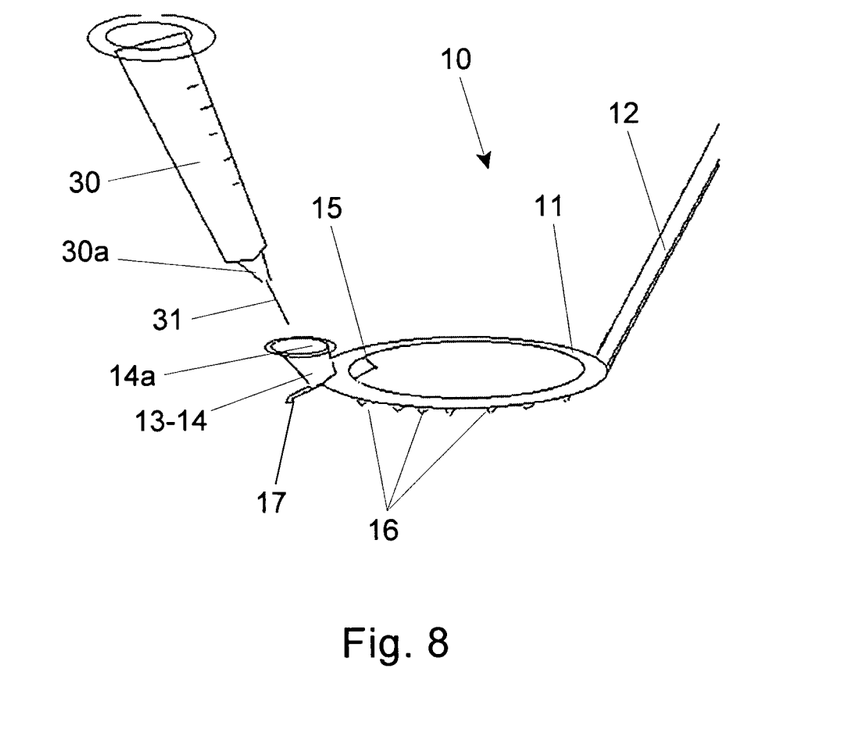
FIG. 8 shows another embodiment of the device according to the invention.
Figure 9:
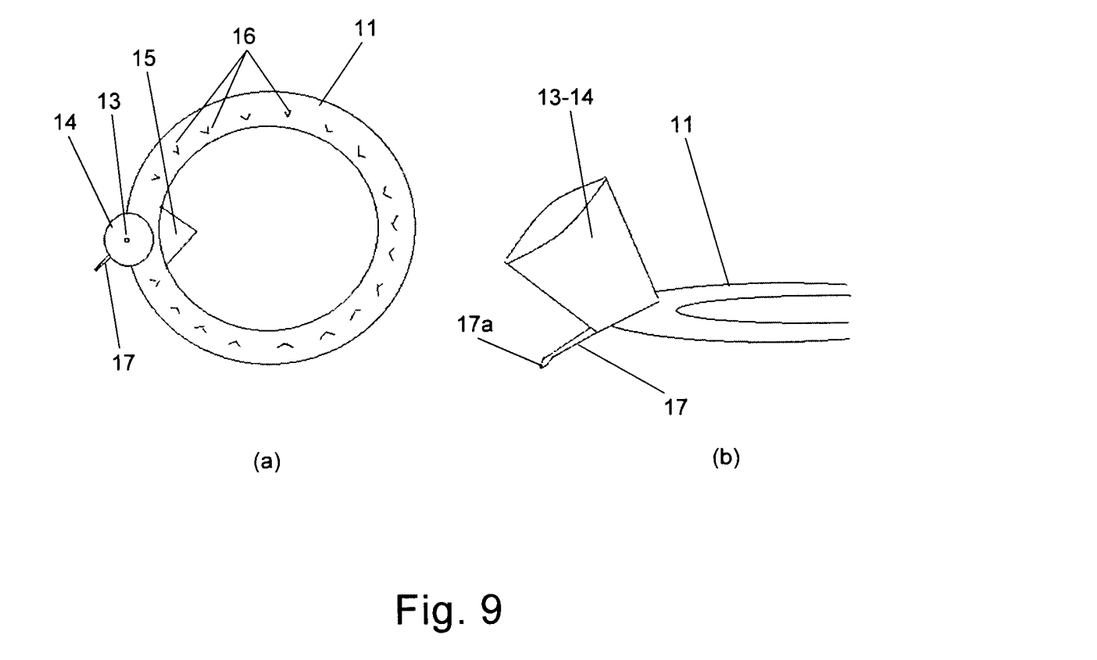
FIGS. 9a and 9b are detail views of the device of FIG. 8.

This drawback is obviated with the embodiment as shown in FIGS. 8, 9a, 9b. The device 10 is to that end provided with a projection 17, which, upon placement of the device on the eyeball, first makes contact with the conjunctiva and moves it a small distance. By subsequently inserting the hypodermic needle 31 into the eye 20 through the moved conjunctiva and the other eye layers and withdrawing it again after administration of the medication, the moved conjunctiva will slide back to its initial orientation relative to the eye 20 and thus cover the injection wound in the underlying eye layers.

The implantation wound is thus no longer in direct contact with the outside environment, so that the risk of intraocular inflammations is significantly reduced. As shown in FIGS. 9a-9b, the projection 17 is provided at the location of the directing means 13-14 in this embodiment. The projection 17 extends towards the eye, and may be provided with a rounded end 17a, so that damage to the conjunctiva is avoided as much as possible.

Figure 10:
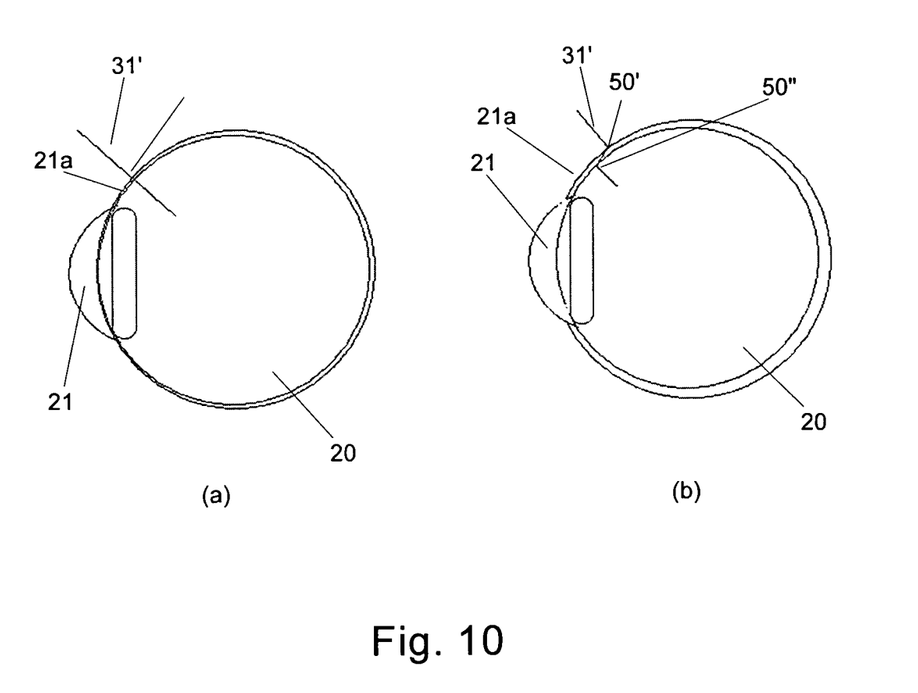
FIGS. 10a and 10b are two plan sketches of the eye of FIG. 7 upon use of the device of FIGS. 8-9a-9b.

FIGS. 10a and 10b show the effect of the moved conjunctiva. In FIG. 10a, the conjunctiva 21a has been moved by the projection 17 of the device 10 according to the invention, and the hypodermic needle 31' causes an implantation wound 50'-50". The moment the hypodermic needle is withdrawn, the conjunctiva 21a will return to its original orientation on the eyeball 21, as a result of which the implantation wound 50' in the conjunctiva will move and the implantation wound 50" in the underlying eye layers is covered by the undamaged conjunctiva. In this way the risk of intraocular inflammations is significantly reduced, if not eliminated.

Figure 11:
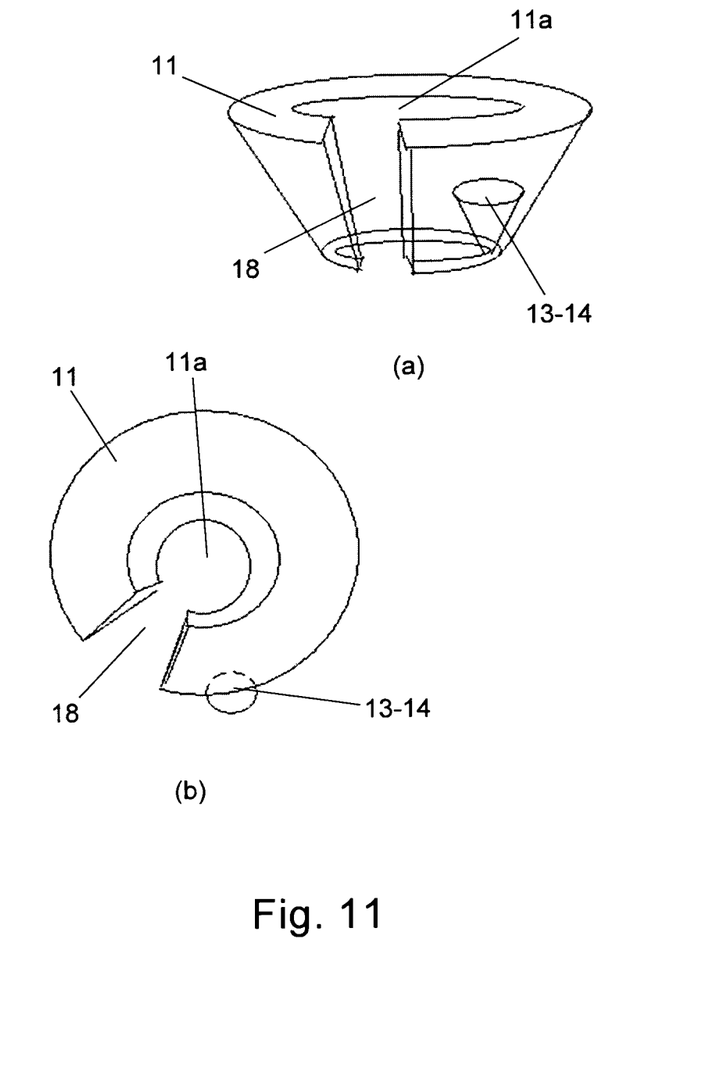
FIGS. 11a-11b show yet another embodiment of the device according to the invention.

In another embodiment as shown in FIGS. 11a-11b, a recess 18 has been formed in the device 10. Via said recess a small puncture can be made in the cornea paracentesis by means of a knife or a needle in order to thus release any intraocular pressure therein. The recess 18 must be sufficiently wide to enable the insertion of a knife or a needle.

It is furthermore noted that the device according to the invention as described herein may also be provided with several bores 13-14 or directing means 15, the different bores 13-14 being adapted to accommodate different needle diameters or for inserting the needle to different depths (for example 3-3.5-4 mm).

It will be understood that, using the tool 10 according to the invention, a more adequate treatment of all kinds of eye disorders, involving the injection of a substance or medicine into the eye 20 by means of a hypodermic needle, can be realised. The tool 10 makes it possible to carry out the medical procedure in a reproducible manner, making all kinds of eye complications and the resulting traumas and inconvenience to the patient a thing of the past.

The invention claimed is:

1. A monolithic hand held manipulation device suitable for intraocular administration of a substance, for example a medication, into a human or animal eye by means of a syringe with a hypodermic needle, said monolithic hand held manipulation device comprising:
   a support element to be placed on the eye,
   said support element including directing means for orienting the hypodermic needle relative to the eye,
   said support element having a frustoconical shape with an apex side and a base side, said frustoconical shaped support element comprising at its apex side an annular support surface to be placed on the eye and an upright frustoconical wall extending from said annular support surface towards its base side,
   wherein the directing means comprises at least one bore formed in the support element and having a perpendicular orientation relative to the eye surface, through which bore the hypodermic needle can be passed and said bore having a diameter corresponding to that of the hypodermic needle, and
   wherein the directing means further comprises an upright edge being raised from said support surface of said support element as well as an end surface forming part of said support surface of said support element, said raised upright edge being provided around the bore and extending in a same orientation as said bore, said raised upright edge forming a space merging into said bore via an end edge and a beveled transition edge for receiving a syringe portion of said syringe,
   said raised upright edge, said end edge and said beveled transition edge functioning as a stop for said syringe portion of said syringe, thus controlling the insertion of the needle into the eye at a single orientation in a reproducible manner and wherein said support element is provided with at least one spreading element to be placed against an eyelid for keeping the eye open.

2. A device according to claim 1, wherein said support element comprises a handle.

3. A device according to claim 2, wherein said handle is built up of two or more arm handles, which are interconnected with a first end and which are provided at different positions on the support element with their other end.

4. A device according to claim 1, wherein the bore will be located at the cornea-sclera transition zone of the eye when the support element is positioned on the eye.

5. A device according to claim 1, wherein the angle between the bore and the eye surface ranges between 70° and 95°.

6. A device according to claim 1, wherein the bore has a diameter corresponding to that of 25 G-30 G hypodermic needles.

7. A device according to claim 1, wherein said support element is provided with friction-increasing means so as to realise a stable position on the eye.

8. A device according to claim 7, wherein said friction-increasing means consist of one or more barbs provided on the support element.

9. A device according to claim 1, wherein the support element is provided with at least one orientation projection to be oriented against the edge of the limbus of the eye.

10. A device according to claim 1, wherein said at least one spreading element is disposed on either side of the support element.

11. A device according to claim 1, wherein said spreading element extends in the plane of the support element.

12. A device according to claim 1, wherein said spreading element has a curved shape.

13. A device according to claim 1, wherein the support element is provided with means arranged for moving the conjunctiva that covers the eye relative to the eye temporarily prior to the insertion of the hypodermic needle into the eye.

14. A device according to claim 13, wherein said moving means are provided at the location of the directing means.

15. A device according to claim 13, wherein said moving means comprise at least one projection directed towards the eye.

16. A device according to claim 15, wherein said projection projects about 1-2 mm.

17. A device according to claim 15, wherein said projection has a beveled end surface.

18. A device according to claim 1, wherein said space transitions into said bore via a bevelled transition edge and an end edge.

19. A device according to claim 18, wherein said end edge extends in an orientation perpendicular to the orientation of the bore between said bevelled edge and said upright edge.

* * * * *